United States Patent [19]

Tonnius et al.

[11] Patent Number: 4,510,090
[45] Date of Patent: Apr. 9, 1985

[54] METHOD FOR THE PRODUCTION OF PHENANTHRENEQUINONE

[75] Inventors: Dietrich Tonnius, Mannheim; Wolfgang Weiss, Neckarhausen; Winfried Orth, Hassloch; Heinrich Miele, Weinheim; Emmerich Pastorek, Hemsbach, all of Fed. Rep. of Germany

[73] Assignee: Rütgerswerke Aktiengesellschaft, Frankfurt, Fed. Rep. of Germany

[21] Appl. No.: 575,128

[22] Filed: Jan. 30, 1984

[30] Foreign Application Priority Data

Feb. 18, 1983 [DE] Fed. Rep. of Germany ....... 3305528

[51] Int. Cl.$^3$ .............................................. C07C 50/16
[52] U.S. Cl. .............................................. 260/396 R
[58] Field of Search ................................... 260/396 R

[56] References Cited

U.S. PATENT DOCUMENTS 3,243,444  3/1966  Sweeny, Jr. .................. 260/396 R
3,479,374  11/1969 Hargis et al. .................. 260/396 R

OTHER PUBLICATIONS

Underwood and Kochmann, J. Am. Chem. Soc., vol. 46, pp. 2069-2071, 9/5/1924.
Oyster and Adkins, J. Am. Chem. Soc., vol. 43, pp. 208-212, 1921.
Wendland and LaLonde, Organic Synthesis, vol. 34, pp. 76-78, 1954.

Primary Examiner—Glennon H. Hollrah
Assistant Examiner—Raymond Covington
Attorney, Agent, or Firm—Beveridge, DeGrandi & Weilacher

[57] ABSTRACT

Improvement of the yield and purity of phenanthrenequinone during its production by oxidation of phenanthrene by means of chromic acid in a sulfuric acidic medium is achieved by preparing a dispersion made up of phenanthrene, alkali dichromate and water at 95°–100° C., cooling said dispersion down to 80°–85° C. and carrying out the oxidation reaction under cooling and portion-wise addition of concentrated sulfuric acid in a temperature range between 80° and 85° C.

4 Claims, No Drawings

METHOD FOR THE PRODUCTION OF PHENANTHRENEQUINONE

The invention relates to the production of 9,10-phenanthrenequinone by oxidation of phenanthrene with chromic acid in a sulfuric acidic medium.

This reaction is known from Organic Synthesis, Vol. 34, p. 76 and from German Patent No. 12 40 065, which are relied upon herein and incorporated by reference.

In the method described in Organic Synthesis the reaction mixture is heated by heat of reaction and the conversion finally takes place under reflux at the boiling point of water. The phenanthrenequinone yields vary between 44 and 48%.

By contrast, according to German Pat. No. 12 40 065 the oxidation occurs at temperatures between 100° and 200° C. under pressure.

According to this method, a substantial increase in the phenanthrenequinone yield is obtained up to 85% of the theoretical yield. However, the resultant phenanthrenequinone still contains 12 to 14% unreacted phenanthrene, which must be isolated in an additional purifying process. Apart from the fact that the method must be carried out under pressure, it also has the drawback that the oxidation reaction does not run its full course.

Therefore, it is the primary object of the present invention to provide a method for the production of phenanthrenequinone that does not exhibit this drawback, that enables the phenanthrene to be completely oxidized without the use of pressure, thereby increasing the yield of phenanthrenequinone.

This object is achieved by the method for the production of 9,10-phenanthrenequinone by oxidation of phenanthrene with the aid of chromic acid by dropwise addition of concentrated sulfuric acid to a mixture of phenanthrene suspended in water and alkali dichromate, a dispersion of phenanthene, alkali dichromate and water being prepared at 95° to 100° C., then cooling the dispersion down to 80° to 85° C. and carrying out the oxidation with cooling and with controlled addition of concentrated sulfuric acid in a temperature range from 80° to 85° C.

In further detail, the present invention is carried out by adding 0.05 to 0.5 grams of a wetting agent per mole phenanthrene is added to the dispersion containing phenanthrene, alkali dichromate and water.

In still further detail, the present invention is carried out by preparing the dispersion of phenanthrene, alkali dichromate and water by mechanical dispersion and maintaining the dispersion during the reaction by mechanical dispersion.

A surprising finding was that the oxidation of phenanthrene occurs readily and completely when a dispersion is prepared at 95°-100° C. comprising water, alkali dichromate and phenanthrene, cooling this dispersion down to 80°-85° C., then starting up the reaction by adding concentrated sulfuric acid and maintaining the reaction temperature in the 80°-85° C. range during the reaction.

It was also found that the required quantity of chromate and sulfuric acid is smaller than was customary in the past, although the oxidation reaction goes farther.

Other surprising advantages of the method of the present invention reside in the fact that the quality of the feedstock is almost irrelevant. The method can also be implemented with low-quality phenanthrene without producing defective charges which, due to excessive resin formations, can no longer be processed. Furthermore, in the method of the invention the phenanthrenequinone no longer accumulates in the form of globules or lumps that enclose organic and inorganic contaminants, but rather as a finely divided crystalline product that can easily be filtered off and washed.

In practice, the method of the invention is carried out by heating a mixture made up of, for example, 1 mole phenanthrene with 1.1 to 2 mole sodium dichromate and 300-700 ml water up to 95°-100° C. and dispersing it by intensive mixing. Any other convenient alkali dichromate may be used for purposes of the invention.

To stabilize the dispersion, small quantities of a wetting agent may be added to the mixture. The addition of a wetting agent permits dispersion at relatively low stirring rates and only moderate agitation during the reaction which then follows. If no wetting agents are employed, the reaction mixture must be held in the dispersed phase during the entire reaction through mechanical dispersal either by means of high-speed agitators or vibrators or by exposure to ultrasonic waves at high frequencies so as to prevent individual particles from settling out by gravity.

Any suitable commercial non-ionic, anionic or cationic auxiliairy agents can be used as wetting agents such as, for example, fatty acid esters, fatty amines, fatty acid amides, polyamines, polyglycolether, carboxylates, fluorinated carboxylates, naphthenates, sulfonates, sulfates, phosphates or quaternary ammonium compounds. These wetting agents are added to the dispersed mixture or the mixture to be dispersed in a quantity from 0.05-0.5 g per mole phenanthrene. Any suitable surface active agent may be used as a wetting agent for purposes of the invention which is capable of stabilizing the dispersion of the phenanthrene, alkali dichromate and water.

The dispersion produced at 95°-100° C. is cooled down to 80°-85° C. Only then is the oxidation reaction initiated by the addition of concentrated sulfuric acid, the reaction mixture being maintained at a temperature of 80°-85° C. by a controlled, metered addition of acid and by external cooling. This process step usually lasts 2 to 3 hours. This is followed by an afterreaction of the strongly acidic reaction mixture lasting approximately one hour at 80°-85° C. Subsequently, the reaction mixture is cooled to 50°-70° C., whereupon the phenanthrenequinone is precipitated and then filtered off, washed, and dried in a manner known in the prior art. The concentration of the sulfuric acid used and the amount thereof are known in the art, such as in Organic Synthesis, Vol. 34, p. 76, and will be apparent to those skilled in the art.

The invention will be further understood by reference of the following examples.

EXAMPLE 1

178 g (86%) phenanthrene are mixed with 500 g $Na_2Cr_2O_7 \cdot 2H_2O$ and 400 g water.

The mixture was reacted with 0.1 g tetraethylammoniumfluoroctane sulfonate and heated up to 100° C. with agitation (180 rpm), then cooled down to 80° C.

Under further agitation, 950 g concentrated sulfuric acid is added within 2 hours and the temperature of the reaction mixture is maintained in a temperature range of 80°-85° C. by external cooling.

Post-agitation is carried out for 1 hour at 85° C., then the mixture is cooled down to 50° C. The precipitated 9,10-phenanthrenequinone is isolated from the sulfuric acidic mother liquor and washed with water until the wash water runs through almost neutral.

After drying, 175.5 g finely divided, crystalline phenanthrenequinone with 92% purity is obtained and a yield 90% of the theoretical yield relative to the phenanthrene charged. The product is free of unreacted phenanthrene.

EXAMPLES 2-6

As in Example 1, phenanthrene is oxidized into phenanthrenequinone with changes in the individual conditions. The following list shows these changes and the yields of phenanthrenequinone obtained in the individual examples.

| Example | Change | Yield/Content |
|---------|--------|---------------|
| 2 | Reaction at 100° C. (without cooling to 80° C.) | 86%/80% |
| 3 | As in Example 2, no wetting agent | 85%/80% |
| 4 | 0.2 g diisobutylnaphthalene sulfonate as wetting agent | 89%/92% |
| 5 | Charging of 82% phenanthrene | 88%/89% |
| 6 | Preparation and maintenance of the dispersion by exposure to ultrasonic waves, no wetting agent | 90%/92% |

Further variations and modifications of the invention will be apparent to those skilled in the art from the foregoing.

We claim:

1. Method for the production of 9,10-phenanthrenequinone by oxidizing phenanthrene with the aid of chromic acid and by controlled addition of concentrated sulfuric acid to a mixture of phenanthrene suspended in water and alkali dichromate, comprising the steps of preparing a dispersion of phenanthrene, alkali dichromate and water at 95°-100° C., cooling said dispersion down to 80° to 85° C. and carrying out the oxidation reaction under cooling and controlled addition of concentrated sulfuric acid in a temperature range from 80° to 85° C.

2. The method as set forth in claim 1, further comprising adding 0.05-0.5 g of a surface active agent per mole phenanthrene to the dispersion of phenanthrene, alkali dichromate and water.

3. The method as set forth in claim 1, further comprising forming said dispersion of phenanthrene, alkali dichromate and water by mechanical dispersion.

4. The method as set forth in claim 3 further comprising initiating the mechanical dispersion during the reaction.

* * * * *